(12) United States Patent
Braun

(10) Patent No.: US 8,981,115 B2
(45) Date of Patent: *Mar. 17, 2015

(54) PROCESS FOR THE SYNTHESIS OF HALOGENATED CYCLIC COMPOUNDS

(71) Applicant: Solvay SA, Brussels (BE)

(72) Inventor: Max Braun, Wedemark (BE)

(73) Assignee: Solvay SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/872,860

(22) Filed: Apr. 29, 2013

(65) Prior Publication Data

US 2013/0237710 A1   Sep. 12, 2013

Related U.S. Application Data

(63) Continuation of application No. 13/120,505, filed as application No. PCT/EP2009/062462 on Sep. 25, 2009, now Pat. No. 8,431,710.

(30) Foreign Application Priority Data

Sep. 30, 2008   (EP) ..................................... 08165547

(51) Int. Cl.
  *C07D 231/16*  (2006.01)
  *C07D 231/12*  (2006.01)
  *C07D 213/803*  (2006.01)
  *C07D 239/36*  (2006.01)

(52) U.S. Cl.
  CPC .......... *C07D 231/12* (2013.01); *C07D 213/803* (2013.01); *C07D 239/36* (2013.01)
  USPC ..................................................... 548/373.1

(58) Field of Classification Search
  CPC ..................................................... C07D 231/16
  USPC ..................................................... 548/373.1
  See application file for complete search history.

(56) References Cited

U.S. PATENT DOCUMENTS

| | | | |
|---|---|---|---|
| 5,235,060 A | 8/1993 | Adams et al. | |
| 5,393,734 A | 2/1995 | Andrea et al. | |
| 5,569,782 A | 10/1996 | Braun et al. | |
| 5,708,174 A | 1/1998 | King et al. | |
| 7,405,328 B2 | 7/2008 | Hausmann et al. | |
| 2006/0084813 A1 | 4/2006 | Hausmann et al. | |
| 2006/0128702 A1 | 6/2006 | Pal et al. | |
| 2008/0269059 A1 | 10/2008 | Ziemer et al. | |
| 2010/0004457 A1* | 1/2010 | Bland et al. | 546/250 |
| 2010/0256390 A1* | 10/2010 | Bowden et al. | 548/374.1 |

FOREIGN PATENT DOCUMENTS

| | | |
|---|---|---|
| DE | 4128828 A1 | 3/1993 |
| EP | 0163280 A1 | 12/1985 |
| GB | 2305174 A | 4/1997 |
| WO | WO 9958594 A1 | 11/1999 |
| WO | WO 02053518 A2 | 7/2002 |
| WO | WO 2004078729 A1 | 9/2004 |
| WO | WO 2006066885 A1 | 6/2006 |
| WO | WO 2007041052 A2 | 4/2007 |
| WO | WO 2009000442 A2 | 12/2008 |
| WO | WO 2010000871 A2 | 1/2010 |
| WO | WO 2010002577 A1 | 1/2010 |
| WO | WO 2010037688 A1 | 4/2010 |
| WO | WO 2011003854 A1 | 1/2011 |
| WO | WO 2011003856 A1 | 1/2011 |
| WO | WO 2011003860 A1 | 1/2011 |

OTHER PUBLICATIONS

U.S. Appl. No. 12/999,673, filed Dec. 12, 2010, Max Bruan, et al.
U.S. Appl. No. 12/999,714, filed Mar. 31, 2011, Max Bruan, et al.
U.S. Appl. No. 12/999,730, filed Mar. 31, 2011, Max Braun, et al.
U.S. Appl. No. 12/999,750, filed Mar. 31, 2011, Max Braun, et al.
Gorbunova, Marine G., et al—"Synthesis and Properties of β-Ethoxyvinyl Polyfluoroalkyl Ketones" Synthesis, 2000, (5), ISSN 0039-7881, pp. 738-742; 5 pgs.

(Continued)

*Primary Examiner* — Joseph Kosack
*Assistant Examiner* — Karen Cheng

(57) ABSTRACT

A process for the manufacture of a cyclic compound of formula (I)

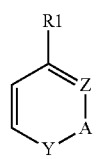

which comprises (a) adding an acid halide of formula $R_1$—C(O)—X, to a vinyl ether of formula (II): $CH_2$=CH—$OR_2$, to produce an addition product, and (b) reacting the addition product with a compound of formula (III): Y-A-Z; wherein $R_1$ is a halogenated alkyl group; wherein X is fluorine, chlorine, or bromine; wherein $R_2$ is an alkyl group, an aralkyl group, or an aryl group; wherein Z and Y designate independently carbon or a heteroatom; and wherein A is a linking group between Z and Y comprising 0, 1, 2 or 3 atoms in the cycle.

10 Claims, No Drawings

(56) References Cited

OTHER PUBLICATIONS

Colla, A., et al—"Trihaloacetylated Enol Ethers : General Synthetic Procedure and Heterocyclic Ring Closure Reactions with Hydroxylamine", Synthesis, 1991, No. 6, pp. 483-486; 4 pgs.

Schlosser, Manfred, et al—"Switchable Reactivity: The Site-Selective Functionalization of Trifluoromethyl-Substituted Pyrazoles"—European Journal of Organic Chemistry, 2002, Issue 17, Wiley VCH Verlag GmbH; pp. 2913-2920; 8 pgs.

Effenberger, Franz, et al—"Die Acylierung von Enolethern mit reaktiven Carbonsäurechloriden" Chemische Berichte, 1982, 115, pp. 2766-2782; 17 pgs; English abstract is provided in this reference.

Galinski, M., et al-; "Differential Double-Layer Capacity of the Carbon-ionic Liquid Interface", Bulgarian Chemical Communications, 2006, vol. 38, No. 3, pp. 192-196; 5 pgs.

Atherton, J., et al—"Cycloaddition Reactions of 2,2,2-trifluorodiazoethane", Journal of the Chemical Society, 1968, [Section] C: Organic , (12), pp. 1507-1513; 7 pgs.

Lang, Robert W., et al-; "Synthesis of Selectively Trifluoromethylated Pyridine Derivatives as Potential Antihypertensives", 1988, Helvetica Chimica Acta 71 (3), pp. 596-601; 7 pgs.

\* cited by examiner

PROCESS FOR THE SYNTHESIS OF HALOGENATED CYCLIC COMPOUNDS

CROSS-REFERENCE TO RELATED APPLICATIONS

This application is a continuation of U.S. nonprovisional application Ser. No. 13/120,505, which is the U.S. national stage entry under 35 U.S.C. §371 of International Application No. PCT/EP2009/062462 filed Sep. 25, 2009, which claims priority to European Application No. 08165547.4 filed Sep. 30, 2008, the whole content of these applications being herein incorporated by reference for all purposes.

TECHNICAL FIELD OF THE INVENTION

The present invention relates to a process for the synthesis of halogenated cyclic compounds.

BACKGROUND

Halogenated cyclic compounds are useful for example as intermediates for the preparation of various herbicides, insecticides, miticides, pesticides etc. U.S. patent application US 2006/0128702 A1 describes the synthesis of 3-trifluoromethyl-1H-Pyrazole (TFPZO) by reacting 4-ethoxy-1,1,1-trifluoro-3-buten-2-one with hydrazine dihydrochloride. Atherton and Fields, J. Chem. Soc. (C), 1968, p.1507-1513 describe the synthesis of 3-trifluoromethyl-1H-Pyrazole from 2,2,2-trifluorodiazoethane. The TFPZO compound is used as intermediate in chemical synthesis. European patent application EP-A-163280 discloses the manufacture of 2-hydroxy-4-trifluoromethyl pyrimidine (TFPMO) from the reaction product of TFAH with EVE. The TFPMO compound is used as intermediate in chemical synthesis, to produce pyrimidinylphosphates as pesticides.

SUMMARY OF THE INVENTION

It is an object of the present invention to provide an efficient process for manufacturing halogenated cyclic compounds, in particular halogenated nitrogen containing heterocycles which allows for good yields and product purities, starting from readily available starting materials.

The invention concerns in consequence a process for the manufacture of a cyclic compound of formula (I):

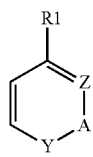

wherein $R_1$ is a halogenated alkyl group
Z and Y designate independently carbon or a heteroatom
A is a linking group between Z and Y comprising 0, 1, 2 or 3 atoms in the cycle which comprises (a) adding an acid halide of formula $R_1$—C(O)—X
wherein X=fluorine, chlorine or bromine and $R_1$ has the meaning given above, to a vinyl ether of formula (II) $CH_2$=CH—$OR_2$ (II) wherein $R_2$ is an alkyl group, an aralkyl group or an aryl group to produce an addition product and (b) said addition product is reacted with a compound of formula (III) Y-A-Z (III), Z, Y and A are as defined above.

DETAILED DESCRIPTION

It has been found, surprisingly, that the addition product of an acid halide, in particular acid chloride with a vinyl ether as specified above is particularly suitable as starting material for producing cyclic compounds as detailed above. Overall yield starting from acid halide and vinyl ether is good. A purification of the addition product may be unnecessary before further reaction. The addition product, in particular if hydrogen halide is present, may increase the reaction rate in the reaction with the compound of formula (III) and allow for easier separation of the cyclic compound produced from the reaction mixture, in particular when a nitrogen-containing heterocycle is produced.

In the process according to the invention, R1 preferably contains at least 1, more preferably 2 fluorine atoms. In one preferred aspect R1 is a perfluoroalkyl group. R1 is often a C1 to C3 halogenated alkyl group, preferably a C1 to C3 fluorinated alkyl group, in particular as described here before. R1 is more preferably a C1 fluorinated alkyl group selected in particular from $CF_3$, $CF_2H$ and $CF_2Cl$. A $CF_3$ group is more particularly preferred.

In another aspect, R1 preferably contains at least 1, more preferably 2 fluorine atoms and at least 1 other halogen atom. R1 is more preferably a fluorinated C1 alkyl group selected in particular from $CF_2Br$ and $CF_2Cl$.

In the process according to the invention, X is often selected from Cl and Br and is more preferably Cl.

Acid halides used in the present invention can be obtained, for example, by photoxidation of halogenated precursor alkanes, in particular as described in U.S. Pat. No. 5,569,782 the contents of which is incorporated by reference in the present application. In particular, trifluoroacetyl chloride, which is a particularly preferred starting material in the present invention, can be obtained by photooxidation of 1,1,1-Trifluoro-2,2-dichloroethane (HCFC-123).

In the process according to the invention, $R_2$ is often selected from a C1 to C4 alkyl group, preferably a methyl, an ethyl, an isopropyl or a n-butyl group and is more preferably an ethyl group.

Consequently, in a most preferred aspect, the acid halide is trifluoroacetyl chloride and the vinyl ether is ethyl vinyl ether or methyl vinyl ether, more preferably ethyl vinyl ether.

In the process according to the invention Z and Y can be independently selected from oxygen, sulphur, nitrogen and carbon. The process according to the invention applies in particularly advantageous manner when at least one of Z and Y is nitrogen.

It is understood that it is appropriate that in the compound Z-A-Y, Z and Y be under a form which enables them to react in the reaction of step (b). For example, suitably, Z and/or Y are selected from —NH2, —NHR3, wherein R3 is an alkyl aryl or aralkyl residue, preferably a C1 to C6 alkyl, or hydrogen halide salts thereof, —OH, —SH and donor carbon atoms for example a CH2 group in α-position to a carbonyl function such as a keto or ester group.

In the process according to the invention, A is a linking group between Z and Y. Such linking group can simply be a covalent bond, in which case A contains 0 atoms. The linking group A can also contain 1, 2 or 3 atoms, which form part of the ring (annular atoms) when A forms part of the structure of compound (I) and which are catenary (i.e. in the chain linking Z and Y) when A forms part of the structure of compound (III). Preferably, A comprises 1 or 2 catenary/annular atoms, in particular, optionally substituted carbon atoms. In the latter case, A is suitably selected from —CH2—, —C(=O)—, —CH2—CH2 and CH2—C(=O)— and —C(=S)—.

Particular examples of compound of formula (III) are selected from hydrazine or its hydrate or hydrochloride, urea, thiourea, malonic acid monoamide (for example methyl or ethyl ester of malonic acid monoamide), and malomononitrile (2-cyano-acetic acid alkyl ester, for example methyl or ethyl ester).

It is understood that the teaching of the present invention enables the skilled person to select the appropriate combination of the various groups R1, Z, Y and A of the formulae (I) and (III) on account of the desired cyclic compound and the known reactivity and valency of the respective groups.

The process according to the invention can be suitably used for the manufacture of the compounds of formula (I) according to the invention corresponding more specifically to one of the formulae

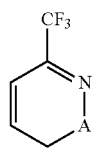
VIII

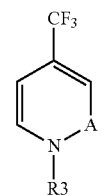
IX

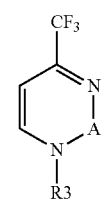
X

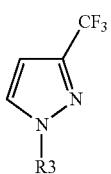
XI wherein A comprises 1 catenary/annular atoms, optionally substituted carbon atoms. In the latter case, A is suitably selected from —CH2—, —C(═O)—, —CH2—CH2 and CH2—C(═O)— and —C(═S)—
wherein R3 is H or a C1 to C6 alkyl.

In the process according to the invention, the reaction of step (b) is generally carried out at a temperature in the range from −15° C. to +80° C., preferably from 0° C. to +20° C.

In the process according to the invention, the reaction of step (b) can be carried out in the presence of a non-hindered amine. Non-hindered amines refer to chemical compounds containing an amine functional group bonded to non-sterically hindering groups. Typical examples of non-sterically hindering groups are short linear aliphatic groups such as methyl, ethyl, propyl and n-butyl. Typical examples of non-hindered amines are for example methylamine, diethylamine, triethylamine and tri-n-butylamine.

Triethylamine is most preferred non-hindered amine.

In the process according to the invention, the molar ratio of the non-hindered amine to the compound of formula (III) is advantageously from 0.5:1 to 1.7:1, preferably from 0.6:1 to 1.5:1, and more preferably from 0.8:1 to 1.2:1. Most preferably, the molar ratio is about 1.

In the process according to the invention, the reaction of step (b) can optionally be carried out in the presence of an additive. Such additive generally increases the polarity of the reaction medium. Ionic liquids can be suitably used as additives. Typical examples of additives are for instance 1,3-dialkylimidazolium or 1,3-dialkyl piridinium salts in particular 1-ethyl-3-methylimidazolium trifluoromethanesulfonate (EMIMOtf). Amines such as 4-Dimethylaminopyridine (DMAP), Diazabicyclo [5.4.0] undec-7-ene (DBU) and Diazabicyclononan (DBN) as such or under salt form, for example as trifluoroacetic acid salt can also be suitably used as additive.

For the purpose of the present invention, the term "ionic liquid" refers to a homogeneous composition consisting of a single salt (one cationic species and one anionic species) or it may refer to a heterogeneous composition containing more than one species of cation and/or more than one species of anion.

In the process according to the invention, the reaction of step (b) is often carried out in an organic solvent, in particular a polar organic solvent. Alcohols such as methanol or ethanol give good results in the reaction of step (b).

Methanol is particularly preferred.

The process according to the invention suitably further comprises isolating the compound of formula (I) from the reaction medium of step (b) by solid/liquid separation, for example filtration or by distillation.

In a first embodiment of the process according to the invention the addition product comprises a compound of formula (IV):

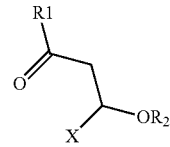

wherein X, R$_1$ and R$_2$ are as defined above.

In a preferred aspect of this first embodiment the addition product comprises a compound of formula (V):

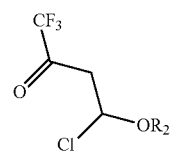

wherein R$_2$ is as defined above.

Compounds of formulae (IV) and (V) can be advantageously used as starting materials to form cyclic compounds, in particular in accordance with the process according to the invention. The invention concerns in consequence also the use of a compound of formula (IV) or (V) as reagent in an addition reaction to form a cyclic compound.

When the addition product comprises a compound of formula (IV) or (V), its content is generally at least 0.1 wt. % relative to the total weight of addition product. Often this content is at least 0.5%. In some embodiments this content does not exceed 10 wt. %.

The addition product can also consist essentially of compound of formula (IV) or (V). In this case its content is generally from 90-99.9, often from 95 to 99.0 wt. % relative to the total weight of addition product.

In a second embodiment of the process according to the invention, the addition product comprises a compound of formula (VI):

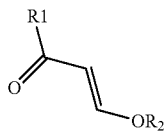

wherein $R_1$ and $R_2$ are as defined above.

In a preferred aspect of the second embodiment, the addition product comprises a compound of formula (VII):

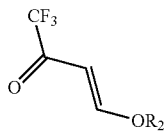

wherein $R_2$ is as defined above.

The compounds of formulae (VI) and (VII) can be obtained preferably by a process comprising (a) adding, as described above, acid halide to vinyl ether to obtain a reaction product comprising compound of formula (IV) or (V) and (b) eliminating hydrogen halide to produce a compound of formula (VI) or (VII) respectively. Such reaction can be carried out in the presence of base such as described in U.S. Pat. No. 5,708,174 or, preferably, in the absence of base such as described in U.S. Pat. No. 7,405,328, the entire contents of said two US patents being incorporated by reference into the present application.

When the addition product comprises a compound of formula (VI) or (VII), its content is generally at least 0.1 wt. % relative to the total weight of addition product. Often this content is at least 0.5%. In some embodiments this content does not exceed 10 wt. %.

The addition product can also consist essentially of compound of formula (VI) or (VII). In this case its content is generally from 90-99.9, often from 95 to 99.0 wt. % relative to the total weight of addition product.

In the process according to the invention, the addition product can be a mixture of compounds of formula (IV) and (VI) or (V) and (VII) respectively. In this case the molar ratio between compounds (IV) and (V) on the one hand and (VI) and (VII) on the other hand is generally from 0.01 to 100, preferably from 0.1 to 10.

In particular, when the addition reaction in the process according to the invention is carried out in the absence of base, it is possible to provide a crude product from the addition reaction (a) to the reaction (b). In addition to the addition product as described here before such crude product may notably contain hydrogen halide, in particular hydrogen chloride.

In one particular embodiment of the process according to the invention, HX, in particular HCl is fed to step (b). In particular such HX, in particular HCl, produced in step (a) may suitably be fed to step (b).

In particular in this embodiment and more particularly when in addition at least one of Z or Y is nitrogen, it has been found that it is possible to precipitate the heterocycle from the reaction medium of step (b) by addition of HX in particular HCl and to isolate it for example by filtration. The HX addition can be carried out, for example during reaction or during work-up.

The invention also concerns a process for the synthesis of a cyclic compound of formula (I):

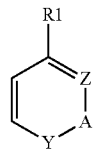

wherein $R_1$ is a halogenated alkyl group
Z and Y designate independently carbon or a heteroatom
A is a linking group between Z and Y comprising 0, 1, 2 or 3 atoms in the cycle
wherein an addition product obtainable by addition of an acid halide of formula $R_1$—C(O)—X wherein X=fluorine, chlorine or bromine and $R_1$ has the meaning given above, to a vinyl ether of formula (II) $CH_2=CH-OR_2$ (II) wherein $R_2$ is an alkyl group, an aralkyl group or an aryl group is reacted with a compound of formula (III) Y-A-Z (III), Z, Y and A are as defined above in the presence of hydrogen halide, in particular hydrogen chloride.

The definitions and preferences described above in the framework of the manufacturing process according to the invention equally apply to the synthesis process.

The following examples are intended to illustrate the invention in further detail without limiting its scope.

EXAMPLES

Example 1

Manufacture of 6-(trifluoromethyl)pyrimidin-2(1H)-on

To a solution of 8.74 moles of urea in 2.2L of methanol in a 3-necked flask, equipped with a mechanical stirrer, a reflux condenser and a dropping funnel was added dropwise over about 3 hours under $N_2$ atmosphere an equimolar amount of 4-ethoxy-1,1,1-trifluoro-3-buten-2-one (ETFBO) which had been manufactured by addition of trifluoroacetyl chloride to ethyl vinyl ether. The temperature of the reaction mixture was kept below 15° C. After 15 min, 1.35 L of a concentrated HCl solution (32%) was added to the cooled suspension obtained and a clear solution was obtained. The solution was slowly heated to 60° C. and after 2 hours stirring, a suspension was formed. After overnight stirring at 60° C. and subsequently 1 h stirring at 0 to 5° C., the precipitate was filtered off. The residue was washed with water until neutral pH and subsequently with hexane (ca. 500 ml). After overnight drying on a rotary evaporator under reduced pressure in a 2-L flask, 6-(trifluoromethyl)pyrimidin-2(1H)-on was obtained as colorless crystals. The yield was 1.2 kg (85% of the theoretical yield).

Example 2

Manufacture of 3-(trifluoromethyl)1H-pyrazole

To a solution of 4.4 moles hydrazine.hydrochloride in 2.2 L of methanol in a 3-necked flask, equipped with a mechanical stirrer, a reflux condenser and a dropping funnel an equimolar amount of ETFBO which had been manufactured by addition of trifluoroacetyl chloride to ethyl vinyl ether was added dropwise over about 4 hours under $N_2$ atmosphere. The temperature of the reaction mixture was kept below 15° C. After 12 h of reflux, the reaction batch was filtered in a 2-L flask and concentrated under vacuum (an identical batch was made under the same conditions, yield of both crude products was ca. 95%). Subsequently, the combined crude product was purified by shortpass-vacuum distillation at 27 mbar. The yield was 1105 g, which corresponded to 92% of the theoretical yield.

Example 3

Manufacture of 6-(trifluoromethyl)pyrimidin-2(1H)-on from CETFBO

Synthesis of CETFBO: 4.0 moles of trifluoroacetyl chloride was condensed in a 3-necked flask which was cooled at around −30° C. during ca. 2 hours. 4.0 moles of ethyl vinyl ether was added dropwise to the liquid trifluoroacetyl chloride cooled at around −30° C. during about 2.5 hours. CETFBO could be obtained quantitatively without any elimination of HCl.

Synthesis of 6-(trifluoromethyl)pyritnidin-2(1H)-on: 0.12 moles of the cooled solution of CETFBO was added dropwise to a stirred solution of 0.1 moles of urea in 25 mL of methanol in a 3-necked flask whereby the temperature was kept below 5° C. The solution was stirred overnight at room temperature. The brown colored solution obtained was then heated at 70° C. for 4.5 hours. Upon cooling the solution in an ice-bath, 6-(trifluoromethyl)pyrimidin-2(1H)-on was obtained as pale beige crystals which were filtered off and washed with water. After drying on a rotary evaporator under reduced pressure, 6-(trifluoromethyl)pyrimidin-2(1H)-on was obtained in 82% yield.

Example 4

Manufacture of 3-pyridinecarboxylic acid, 1,2-dihydro-2-oxo-6-(trifluoromethyl)-methyl ester (MTFP-MOC)

420 mmoles of methyl malonate monoamide (MMA) was added to ice cooled triethylamine (420 mmoles) over a period of about 20 min under vigorous stirring. ETFBO which had been manufactured by addition of TFAC to ethyl vinyl ether, was then added dropwise under ice cooling and over a period of about 30 min whereby the temperature of the reaction mixture was kept under 10° C. The reaction mixture was then further stirred at room temperature for 20 h. A concentrated HCl solution (2N) was added to the solution until a pH of 3 was obtained. After extraction of the solution with ethyl acetate, the organic phase was washed with water and dried over sodium sulfate. After removing the volatile compounds on a rotary evaporator, the crude product could be obtained in 86% yield. After crystallization from methanol/water, MTFPMOC was obtained with a purity>98% (GC).

Example 5

Manufacture of 3-Pyridinecarboxylic acid, 1,2-dihydro-2-oxo-6-(trfluoromethyl)-ethyl ester (ETFP-MOC)

420 mmoles of ethyl malonate monoamide (EMA) was added to ice cooled triethylamine (420 mmoles) over a period of about 20 min under vigorous stirring. ETFBO which had been manufactured by addition of TFAC to ethyl vinyl ether, was then added dropwise under ice cooling and over a period of about 30 min whereby the temperature of the reaction mixture was kept under 10° C. The reaction mixture was then further stirred at room temperature for 20 h. A concentrated HCl solution (2N) was added to the solution until a pH of 3 was obtained. After extraction of the solution with ethylacetate, the organic phase was washed with water and dried over sodium sulfate. After removing the volatile compounds on a rotary evaporator, the crude product could be obtained in 86% yield. After crystallization from methanol/water, ETFPMOC was obtained with a purity >98% (GC).

The invention claimed is:

1. A process for the manufacture of a cyclic compound of formula (XI):

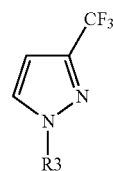

wherein R3 is H or a C1 to C6 alkyl;
said process comprising:
(a) adding CF3C(O)—Cl to a vinyl ether of formula (II): $CH_2$=CH—$OR_2$, wherein $R_2$ is selected from the group consisting of an alkyl group, an aralkyl group, and an aryl group, to produce an addition product, and wherein the addition reaction of step (a) is carried out in absence of a base; and
(b) reacting said addition product with a compound of formula (III): Y-A-Z,
wherein Z and Y are independently selected from —NHR3 in which R3 is H or a C1 to C6 alkyl as defined above, and wherein A is a covalent bond and contains zero atoms; and wherein the addition product supplied to step (b) is a crude product from step (a).

2. The process of claim 1, wherein R3 is H.

3. The process according to claim 1, wherein the addition product comprises a compound of formula (V):

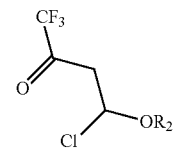

wherein $R_2$ is selected from the group consisting of an alkyl group, an aralkyl group, and an aryl group.

4. The process according to claim 1, wherein the addition product comprises a compound of formula (VII):

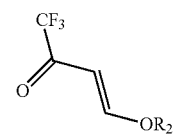

wherein $R_2$ is selected from the group consisting of an alkyl group, an aralkyl group, and an aryl group.

5. The process according to claim 1, wherein $R_2$ is a C1 to C4 alkyl group.

6. The process according to claim 1, wherein $R_2$ is an ethyl group.

7. The process according to claim 1, wherein the compound of formula (III) is selected from the group consisting of hydrazine, hydrazine hydrate, and hydrazine hydrochloride.

8. The process according to claim 1, wherein HCl produced in step (a) is fed to step (b).

9. The process according to claim 1, wherein the reaction of step (b) is carried out at a temperature in the range from −15° C. to +80° C.

10. The process according to claim 1, further comprising isolating the compound of formula (XI) from the reaction medium of step (b) by solid/liquid separation or distillation.

* * * * *